(12) United States Patent
Oudenhoven et al.

(10) Patent No.: US 9,498,148 B2
(45) Date of Patent: Nov. 22, 2016

(54) ELECTRODE FOR BIOPOTENTIAL SENSING

(71) Applicant: Stichting IMEC Nederland, Eindhoven (NL)

(72) Inventors: Jozef Franciscus Maria Oudenhoven, Eindhoven (NL); Vojkan Mihajlovic, Eindhoven (NL); Marcel Zevenbergen, Nuenen (NL)

(73) Assignee: Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 14/972,661

(22) Filed: Dec. 17, 2015

(65) Prior Publication Data

US 2016/0174859 A1    Jun. 23, 2016

(30) Foreign Application Priority Data

Dec. 17, 2014  (EP) .................................... 14198435

(51) Int. Cl.
| | |
|---|---|
| *A61B 5/0478* | (2006.01) |
| *A61B 5/0402* | (2006.01) |
| *A61B 5/0476* | (2006.01) |
| *A61B 5/053* | (2006.01) |
| *A61B 5/04* | (2006.01) |
| *A61B 5/00* | (2006.01) |

(52) U.S. Cl.
CPC ............... *A61B 5/0478* (2013.01); *A61B 5/04* (2013.01); *A61B 5/0402* (2013.01); *A61B 5/0476* (2013.01); *A61B 5/053* (2013.01); *A61B 5/6814* (2013.01); *A61B 2562/046* (2013.01); *A61B 2562/125* (2013.01)

(58) Field of Classification Search
CPC ........................... A61B 5/0478; A61B 5/6814
See application file for complete search history.

(56) References Cited

U.S. PATENT DOCUMENTS

| | | | | |
|---|---|---|---|---|
| 6,757,556 B2* | 6/2004 | Gopinathan | ......... | A61B 5/0002 600/372 |
| 8,548,554 B2* | 10/2013 | Popescu | ............... | A61B 5/0478 600/383 |
| 9,237,857 B2* | 1/2016 | Guger | .................. | A61B 5/0478 |
| 2011/0074396 A1* | 3/2011 | Liao | .................... | A61B 5/04085 324/121 R |
| 2015/0238100 A1* | 8/2015 | Lin | ...................... | A61B 5/0478 600/393 |

OTHER PUBLICATIONS

Chen, Y.H. et al., "Comb-Shaped Polymer-Based Dry Electrodes for EEG/ECG Measurements with High User Comfort", 35th Annual International Conference of the IEEE EMBS, Osaka, Japan, Jul. 3-7, 2013, pp. 551-554.

* cited by examiner

*Primary Examiner* — Lee S Cohen
(74) *Attorney, Agent, or Firm* — McDonnell Boehnen Hulbert & Berghoff LLP

(57) ABSTRACT

An electrode for biopotential sensing comprising a main electrode base and at least a plurality of contact pins protruding from the main electrode base and configured to make contact with a subject's skin. Each of the first plurality of contact pins comprises at least one conductive mesh having an elongated pillar shape. A headset or biopotential monitoring system comprising such an electrode for biopotential sensing.

16 Claims, 14 Drawing Sheets

ELECTRODE FOR BIOPOTENTIAL SENSING

CROSS-REFERENCE TO RELATED APPLICATIONS

The present application is a non-provisional patent application claiming priority to European Patent Application No. 14198435.1 filed Dec. 17, 2014, the contents of which are hereby incorporated by reference.

FIELD OF THE DISCLOSURE

The present description relates generally to electrodes and more specifically to dry-contact electrodes for biopotential sensing.

BACKGROUND

Analysis of biopotential electrical signals generated inside the human body, for example for electrocardiography (ECG), electro-encephalography (EEG), and analysis of the response of biological tissue to imposed currents, for example for bio-impedance measurements, requires a good electrode-to-skin contact. Solutions such as gel electrodes may ensure a good contact between the electrode and the skin with the use of conductive gels. These gels, however, require application before measurements and removal after use, and tend to dry out over time, making them cumbersome and unsuitable for certain applications, such as long time monitoring.

Alternatively, known dry or dry-contact electrodes are currently available in the form of electrodes with rigid pins that are pressed onto the skin. Their rigidity, however, makes such electrodes uncomfortable to wear and prone to motion artifacts. There has been also some interest in developing conductive polymer electrodes, such as the ones described in "*Comb-shaped Polymer-based Dry Electrodes for EEG/ECG Measurements with High User Comfort*", by Y. H. Chen et al., IEEE Engineering in Medicine and Biology Society (EMBC), 35th Annual International Conference of the IEEE, pp. 551-554, Osaka, Japan, Jul. 3-7, 2013. Although such electrodes present promising results, their conductivity is still low for certain applications.

There is a motivation to improve current state of the art dry electrodes in order to improve user comfort, setup time, and/or high quality biopotential measurement.

SUMMARY

Example methods and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. In the following detailed description, reference is made to the accompanying figures, which form a part thereof. In the figures, similar symbols typically identify similar components, unless context dictates otherwise. Other embodiments may be utilized, and other changes may be made, without departing from the scope of the subject matter presented herein.

The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

A new and improved dry-contact electrode is herein proposed, which provides good skin contact and is flexible for improved user comfort. According to an exemplary embodiment the new electrode is used for dry-contact biopotential measurement applications and provides good electrical conductivity even when applied to skin surfaces covered with hair, such as, for example the human scalp. According to an exemplary embodiment the new dry electrode is robust and suitable for long term biopotential measurements. According to an exemplary embodiment the new dry-contact electrode may reduce biopotential measurement artifacts caused, for example, by the non-constant and non-equal pressure on the contact points of electrodes to the skin surface.

According to an exemplary embodiment, an electrode for biopotential sensing is provided, comprising a main electrode base and at least a first plurality of contact pins protruding from the main electrode base and intended for making contact with a subject's skin, and wherein each pin of the first plurality of contact pins comprises a conductive mesh having an elongated pillar shape. According to an exemplary embodiment, the conductive mesh may have, for example, a cylindrical shape, with circular or elliptic cross-section, or a substantially cylindrical shape with one crease. The elongated pillar shape conductive mesh may also have a rectangular or hexagonal prism shape and the pillar may have a regular or irregular polygonal cross-section.

According to an exemplary embodiment, the conductive mesh may be a woven fabric comprising a plurality of conductive wires or fibers designed for being flexible and ensuring conductivity of the pins.

According to an exemplary embodiment, the elongated pillar shape conductive mesh has a width between 1 and 2.5 mm and a length which is greater than the width.

According to an exemplary embodiment the electrode pins consist of the elongated pillar shape conductive mesh with a hollow core.

According to an exemplary embodiment, the cylindrical conductive mesh has a resistance lower than 100 mΩ/cm.

According to an exemplary embodiment, the first plurality of contact pins further comprise a tip which is configured to be in contact with the conductive mesh and the subject's skin.

According to an exemplary embodiment, the tip is covered with a non-polarizable electrode material.

According to an exemplary embodiment, the non-polarizable electrode material further comprises a mixture of materials containing ions that are also present in biological fluids.

According to an exemplary embodiment, the tip is designed for being rigid and with a spherical, hemispherical or conical shape.

According to an exemplary embodiment, the core of the conductive mesh is hollow.

According to an exemplary embodiment, the contact pins comprise two or more conductive meshes having an elongated pillar shape.

According to an exemplary embodiment, the core of the conductive mesh comprises a flexible core material.

According to an exemplary embodiment, the flexible core material is an elastic and/or compressible material, such as a foam and/or a polymer.

According to an exemplary embodiment, the flexible core material further comprises additives which make such material conductive.

According to an exemplary embodiment, the main electrode base is made of a conductive material or a non-conductive material which contains a conductor that makes the contact with each of the pins and conductive meshes.

According to an exemplary embodiment, the first plurality of contact pins contains four or more pins.

The present description also relates to a headset or biopotential monitoring system comprising an electrode for biopotential sensing according to any of the embodiments defined by the claims.

According to an exemplary embodiment, an electrode for biopotential sensing is provided, comprising a main electrode base and at least a first plurality of contact pins protruding from the main electrode base and intended for making contact with a subject's skin, and wherein the first plurality of contact pins comprise a cylindrical conductive mesh. According to an exemplary embodiment, the cylindrical conductive mesh may be a woven fabric comprising a plurality of conductive wires or fibres designed for being flexible and ensuring conductivity of the pins. According to an exemplary embodiment, the cylindrical conductive mesh has a diameter between 1 mm and 1 cm and a length of at least 2 mm. According to an exemplary embodiment, the cylindrical conductive mesh has a resistance lower than 100 mΩ/cm. According to an exemplary embodiment, the first plurality of contact pins further comprise a tip which is configured to be in contact with the subject's skin. According to an exemplary embodiment, the tip is covered with a non-polarizable electrode material. According to an exemplary embodiment, the non-polarizable electrode material further comprises a mixture of materials containing ions that are also present in biological fluids. According to an exemplary embodiment, the tip is designed for being rigid and with a spherical, hemispherical or conical shape. According to an exemplary embodiment, the core of the cylindrical conductive mesh is hollow. According to an exemplary embodiment, the core of the cylindrical conductive mesh comprises more cylindrical conductive mesh layers. According to an exemplary embodiment, the core of the cylindrical conductive mesh comprises a flexible core material.

BRIEF DESCRIPTION OF THE FIGURES

The above and other aspects of the system according to the present description will be shown and explained with reference to the non-restrictive example embodiments described hereinafter.

DETAILED DESCRIPTION

In the following, in the description of exemplary embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the main claim. Furthermore, combinations of features of different embodiments are meant to be within the scope of the invention, as would be clearly understood by those skilled in the art. Additionally, in other instances, well-known methods, structures and techniques have not been shown in detail in order not to obscure the conciseness of the description.

Figure 1:
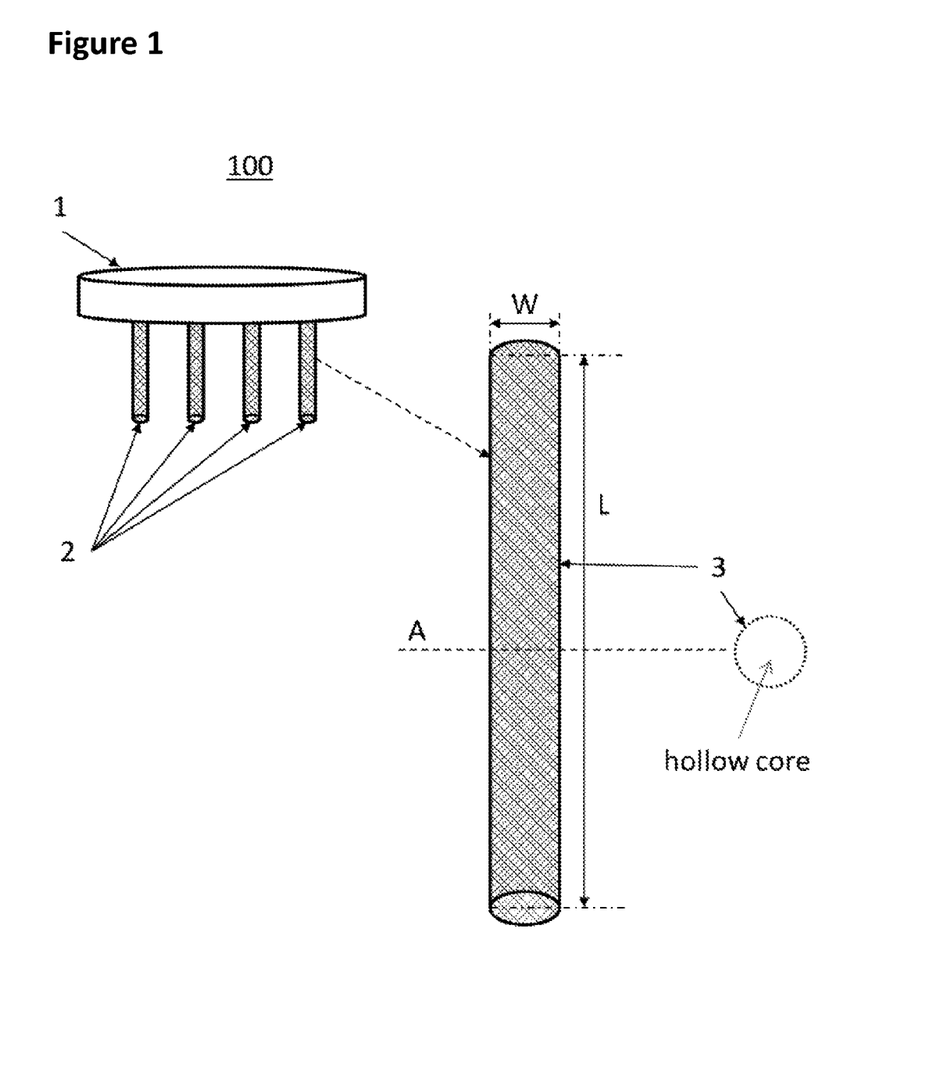
FIG. 1 illustrates an exemplary electrode for biopotential sensing.

FIG. 1 shows a perspective side view of an exemplary electrode 100 for biopotential sensing. The electrode 100 comprises a main electrode body or base 1 and a plurality of contact pads or pins 2 protruding from the main electrode base. According to an exemplary embodiment the electrode comprises at least four pins. The plurality of pins 2 protrude in the direction of the measurement surface or skin when the electrode 100 is applied on the subject, e.g. an area of the subject's skin, for measurement purposes. The main electrode base 1 serves as mechanical support for the pins 2 and is adapted for providing electrical contact between the pins and other electrical/electronic parts of a system for monitoring and processing the sensed biopotential signals (not shown). The main electrode base 1 may be made of a conductive material (e.g. a metal or a conductive polymer) or a non-conductive material which contains one or more conductive lines that make contact with each of the pins 2. Such main electrode base 1 may have, but is not limited to, a disc shape. According to an exemplary embodiment, the electrode pins 2 comprise at least one conductive mesh 3 with an elongated pillar shape. According to an exemplary embodiment, the electrode pins 2 consist of such an elongated pillar shape conductive mesh 3 with a hollow core. According to an exemplary embodiment, the conductive mesh 3 has a cylindrical shape. According to an exemplary embodiment the cylindrical conductive mesh 3 has a circular cross-section (along the line A). According to an exemplary embodiment the conductive mesh 3 is a woven fabric comprising a plurality of conductive wires or fibres, similar to a web or net, that ensures conductivity of the pins. According to an exemplary embodiment the conductive mesh may be a conductive fabric known in the field of electronic shielding. According to an exemplary embodiment, the elongated pillar shape conductive mesh 3 has a width W between 1 and 2.5 mm and a length L which is greater/longer than the width. According to an exemplary embodiment, the resistance of the conductive mesh is lower than 100 mΩ/cm. According to an exemplary embodiment, the pins provide flexibility to ensure a continuous mechanical contact of the conductive mesh with the skin, thereby providing a good mechanical skin-electrode-contact and or more comfort to the user. According to an exemplary embodiment, the length of the pin is greater than its width, which makes it suitable for biopotential electrode sensing applications.

Figure 2:
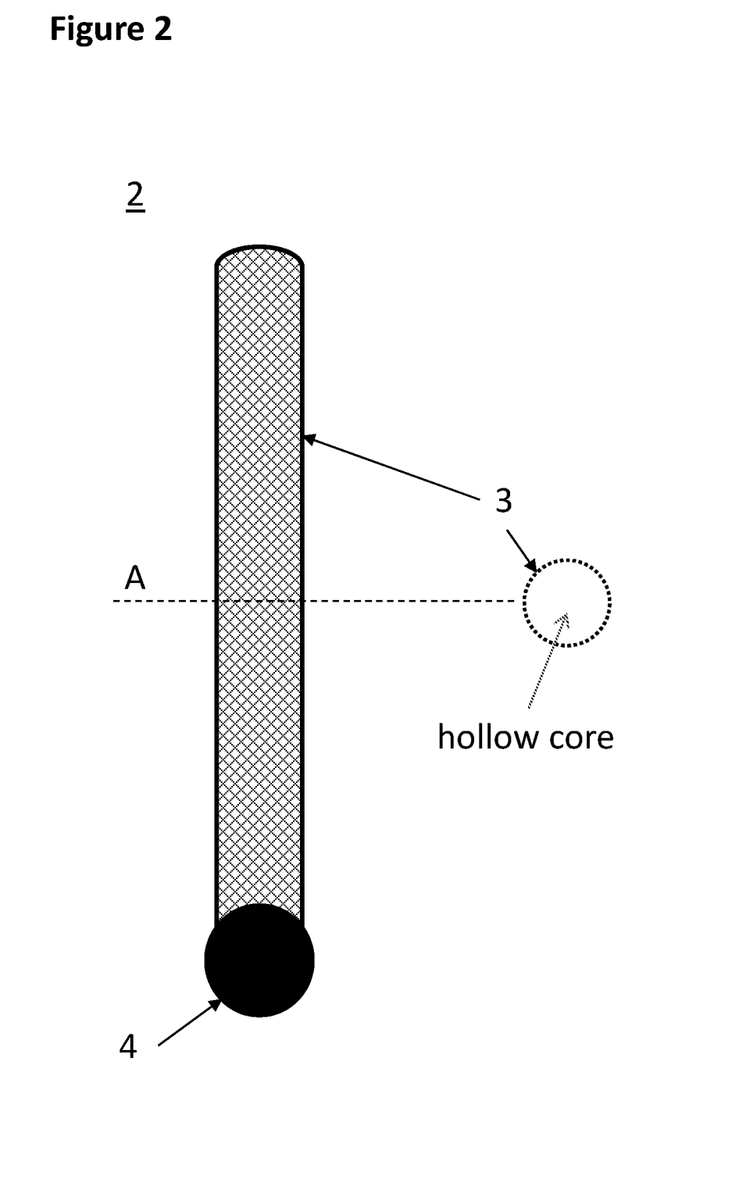
FIG. 2 shows a second exemplary implementation of a pin included in an electrode for biopotential sensing.

FIG. 2 shows a second exemplary implementation of a pin 2 included in an electrode 100 for biopotential sensing. The electrode pins 2 are made of a cylindrical conductive mesh 3 with a hollow core (as in FIG. 1) and comprise an additional spherical-shape tip 4, which will be in contact with the subject's skin. According to an exemplary embodiment, the shape of the tip is designed in such way that it eases penetration between hair, for example with a (hemi-) spherical shape for small diameter pins or non-dense hair. The tip of the pins may also have, but is not limited to, a conical shape (or a cone with rounded off tip). According to an exemplary embodiment, the tip of the electrode is covered with a non-polarizable electrode material, which may provide a good electronic skin-contact, that is, allows a good charge-transfer from the skin to the electrode and vice-versa. Such non-polarizable electrode material may be, but is not limited to, silver (Ag) or silver chloride (AgCl). According to another exemplary embodiment, the non-polarizable material comprises a mixture of materials containing ions that are also present in biological fluids. According to an exemplary embodiment, the electrode pin 2 is designed to be flexible while the pin tip 4 is rigid, which allows for a tip layer to be more than 1 mm so wear will not change the electrode properties, making this a durable and re-usable electrode design. With this method, the mechanical contact to the skin (provided by the flexibility of the pins 2) and the electrical contact (provided by the rigid tip 4) are separated, and can be optimized separately.

Figure 3:
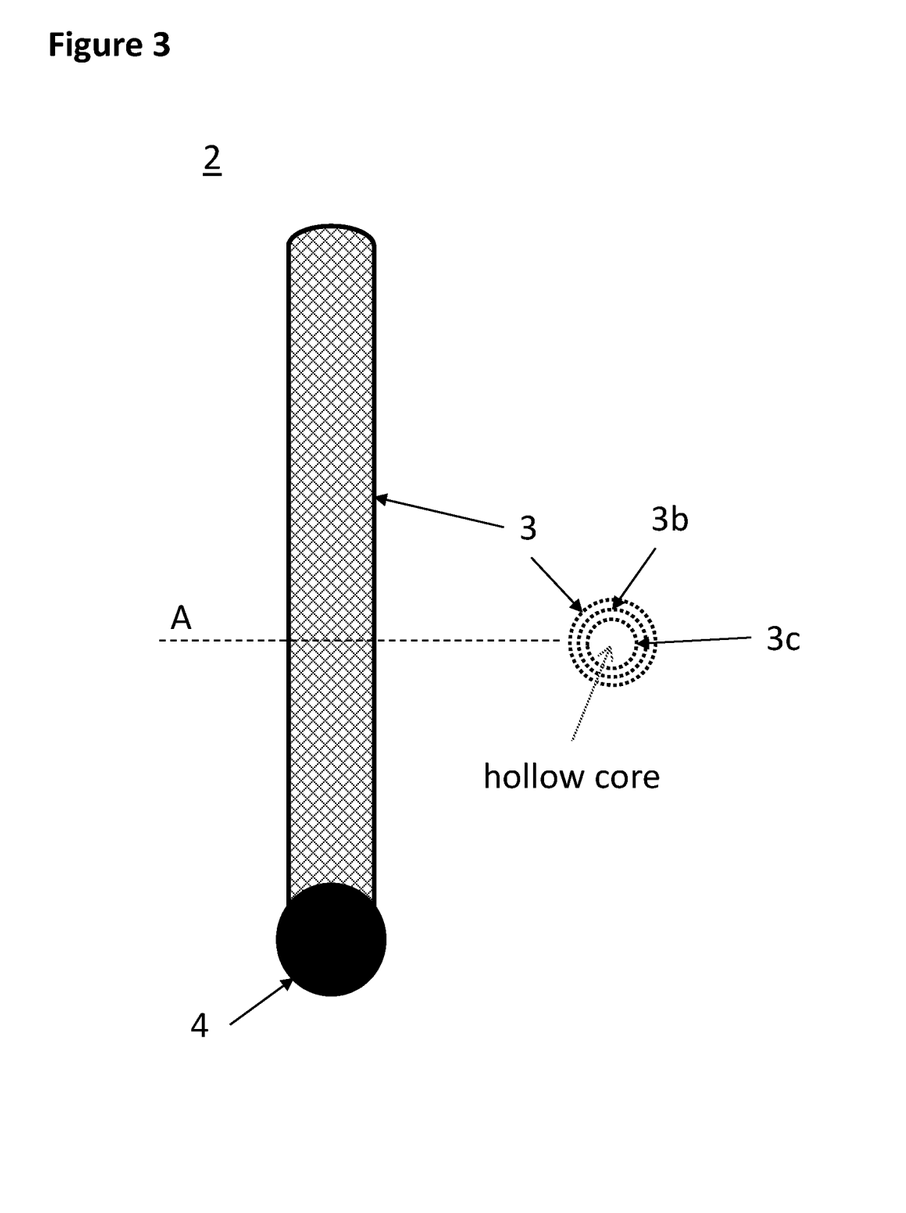
FIG. 3 shows a third exemplary implementation of a pin included in an electrode for biopotential sensing.

FIG. 3 shows a third exemplary implementation of a pin 2 included in an electrode 100 for biopotential sensing. The electrode pins 2 are made of a plurality of cylindrical conductive mesh layers 3, 3b and 3c with a hollow core and comprise an additional spherical-shape tip 4.

Figure 4:
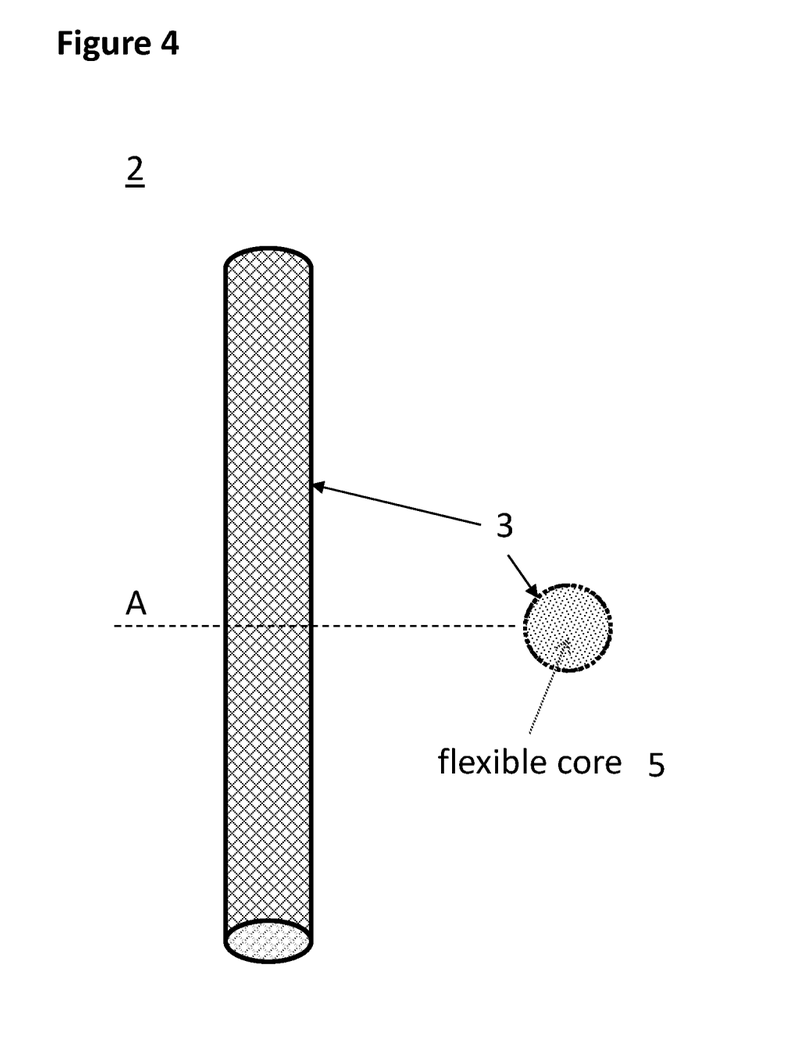
FIG. 4 shows a fourth exemplary implementation of a pin included in an electrode for biopotential sensing.

FIG. 4 shows a fourth exemplary implementation of a pin 2 included in an electrode 100 for biopotential sensing. The electrode pins 2 are made of a cylindrical conductive mesh 3 surrounding a flexible core material 5. The flexible core material of the pins may include an elastic and compressible material. According to an exemplary embodiment, the flexible core material is a polymer. According to an exemplary embodiment, the flexible core material may be, for example, a foam or rubber, such as polystyrene 'Styrofoam'. According to an exemplary embodiment, the flexible core material may comprise additives which make this core material conductive.

Figure 5A:
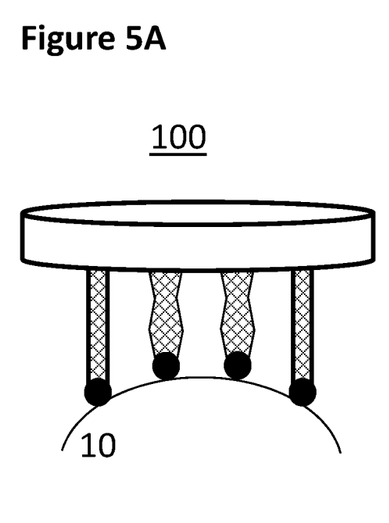
FIGS. 5A and 5B show some generic application examples of exemplary electrodes for biopotential sensing.
Figure 5B:
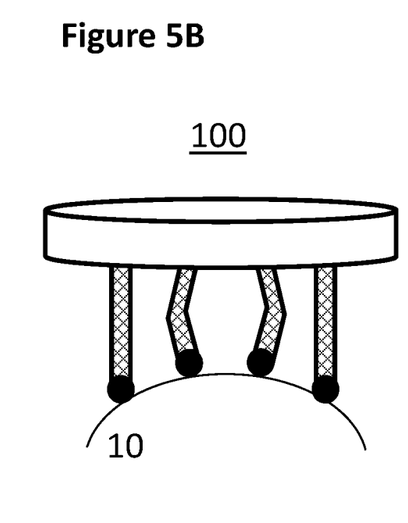

FIGS. 5A and 5B show some exemplary embodiments of electrodes for biopotential sensing. When a multiple pin electrode 100 according to exemplary embodiments is applied to a curved surface 10, the curvature is accommodated by compression or bending of the pins, i.e. the electrode pins will be compressed and make good skin contact. Moreover, with the flexible pins, the user comfort level will be increased, and vibrations of the electrode holder will be dampened, reducing the number of motion artifacts.

Figure 6A:
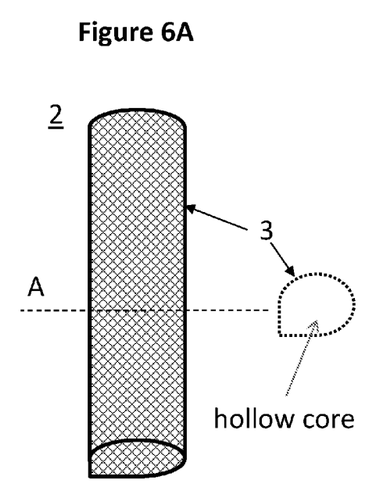
FIGS. 6A, 6B, 6C, and 6D show further exemplary implementations of pins included in an electrode for biopotential sensing.
Figure 6B:
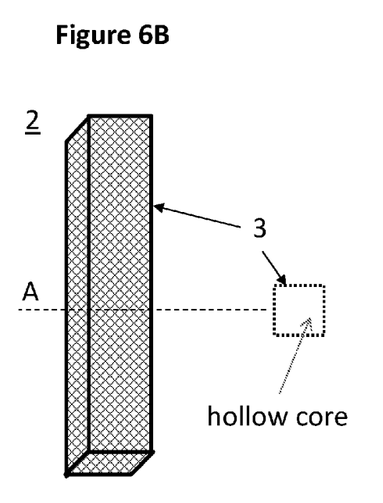
Figure 6C:
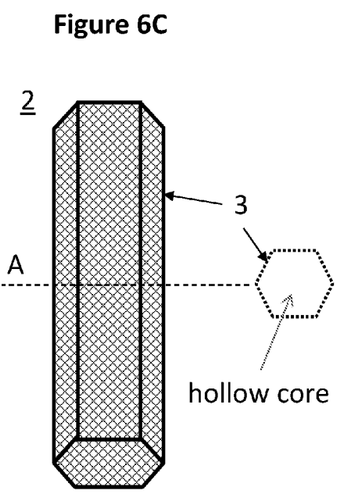
Figure 6D:
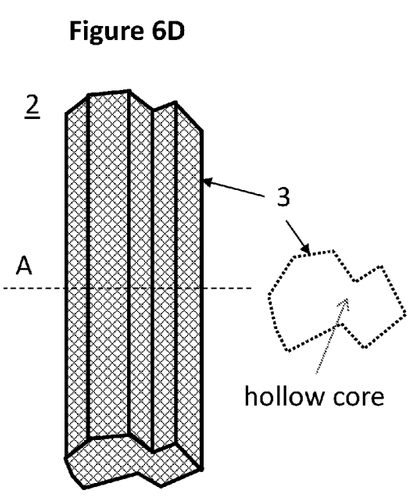

FIGS. 6A, 6B, 6C and 6D show further exemplary implementations of pins included in an electrode for biopotential sensing. FIG. 6A shows a fifth exemplary implementation of a pin 2 included in an electrode 100 for biopotential sensing having a conductive mesh 3 with a substantially cylindrical shape with a crease. FIG. 6B shows a sixth exemplary implementation of a pin 2 included in an electrode 100 for biopotential sensing having a conductive mesh 3 with a rectangular prism shape and a square cross-section. FIG. 6C shows a seventh exemplary implementation of a pin 2 included in an electrode 100 for biopotential sensing having a conductive mesh 3 with a hexagonal prism shape. FIG. 6D shows an eighth exemplary implementation of a pin 2 included in an electrode 100 for biopotential sensing having a conductive mesh 3 with a prism shape and an irregular decagon cross-section. It shall be understood that the elongated pillar shapes of FIGS. 6A to 6D are just examples and the cross-section of the elongated pillar shape may be a regular or irregular polygon.

Figure 7:
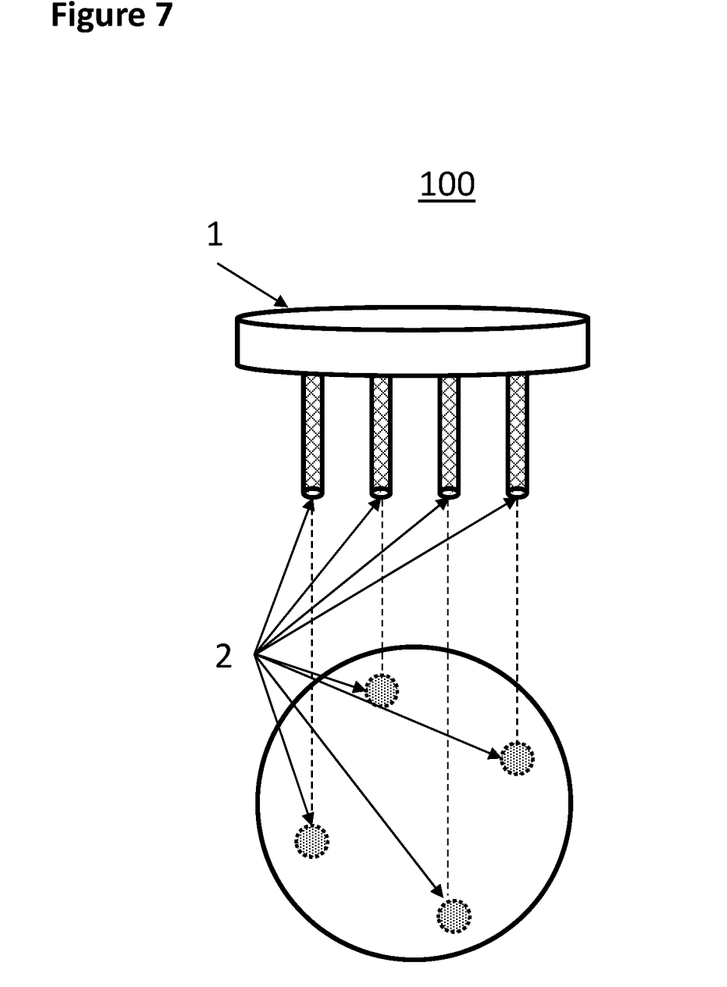
FIG. 7 illustrates a top view of an exemplary electrode for biopotential sensing.

FIG. 7 illustrates a top view of an exemplary electrode 100 for biopotential sensing. The electrode comprises a main electrode body or base 1 and four contact pads or pins 2 protruding from the main electrode base.

Figure 8:
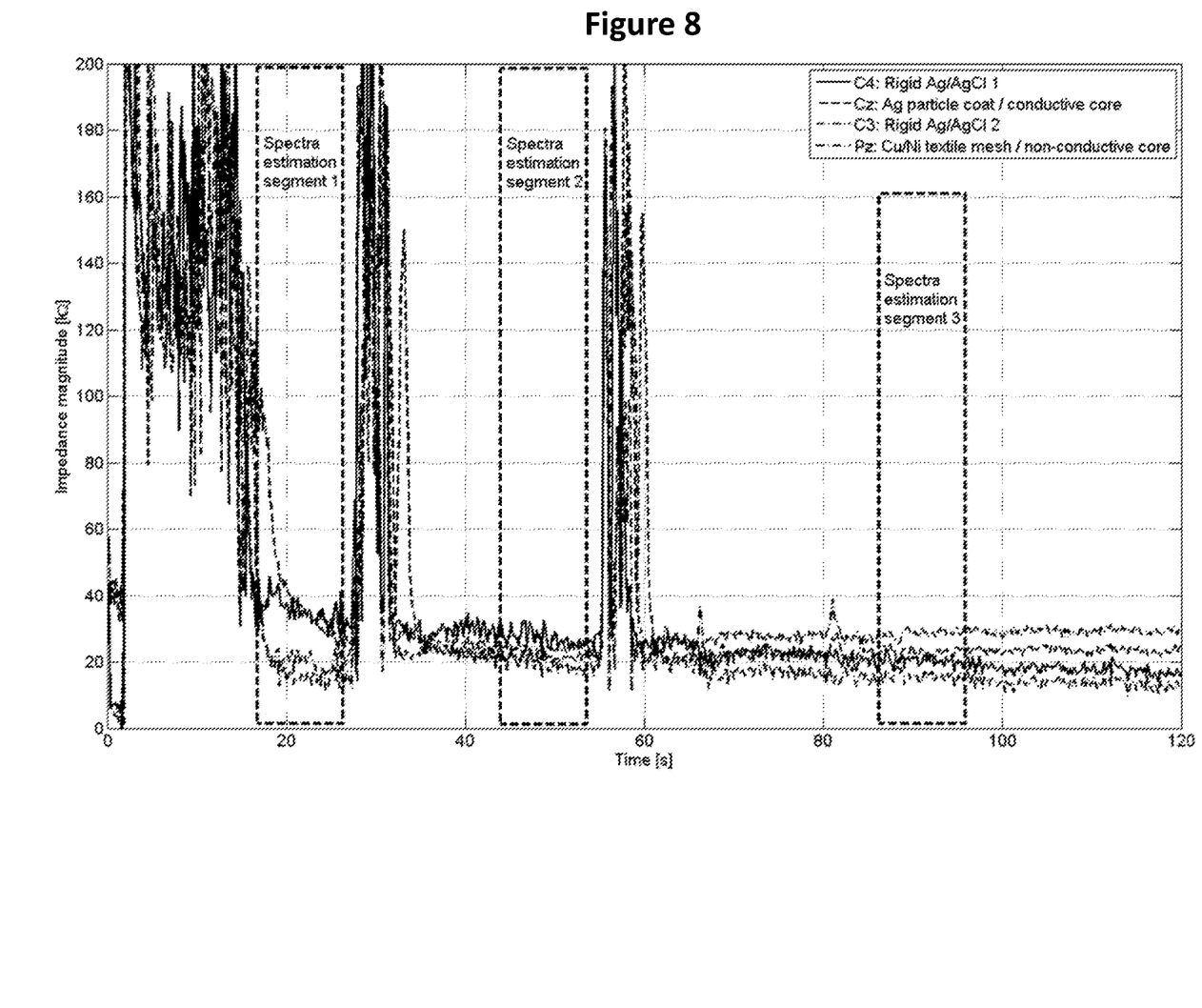
FIG. 8 shows a first graph of impedance values over time presented by a plurality of electrodes for biopotential sensing in comparison to an exemplary electrode for biopotential sensing.

FIG. 8 shows a first graph of impedance values over time presented by a plurality of electrodes for biopotential sensing in comparison to an exemplary electrode for biopotential sensing according to the present description. The impedance values are shown during the first 120 seconds after applying a headset comprising an electrode for biopotential sensing to the head of a subject. Initial large impedance values can be seen when placing the headset on the subject and when readjusting the headset at about 30 and 60 seconds. Overall, the measured impedance for an exemplary electrode for biopotential sensing with a conductive mesh according to the present description is higher (around 20 kOhm) than the one measured with rigid electrodes (around 10 kOhm), but still quite low. The three spectra estimation segments 1, 2 and 3 correspond to the spectral power graphs shown in FIGS. 10, 11 and 12.

Figure 9:
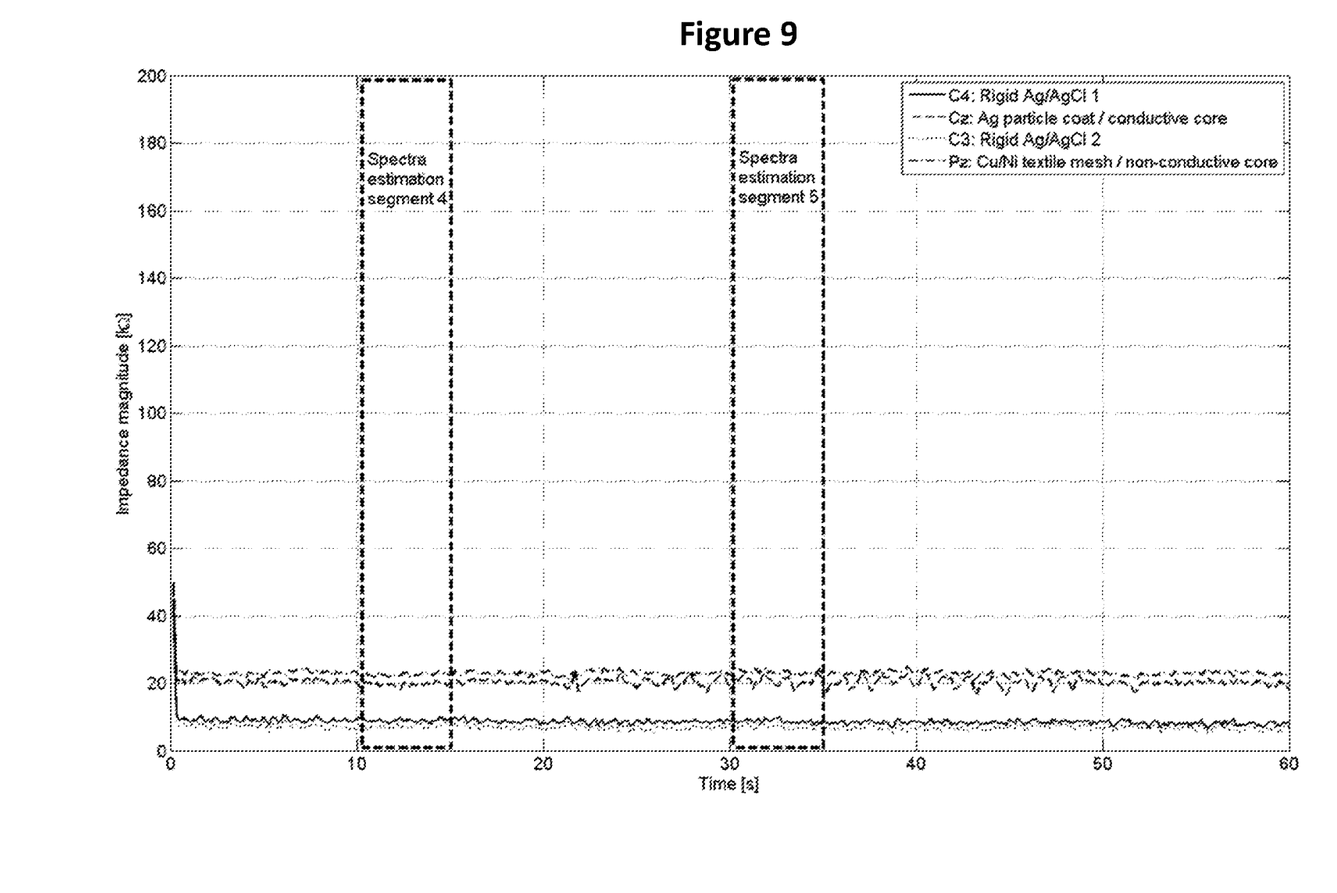
FIG. 9 shows a second graph of impedance values over time presented by a plurality of electrodes for biopotential sensing in comparison to an exemplary electrode for biopotential sensing.

FIG. 9 shows a second graph of impedance values over time presented by a plurality of electrodes for biopotential sensing in comparison to an exemplary electrode for biopotential sensing according to the present description. The impedance values are shown during a 60 second segment starting around 3 minutes after positioning the headset on the subject. The graph shows that the impedance values are more stable and that it is higher (around 20 kOhm) for an exemplary electrode for biopotential sensing with a conductive mesh according to the present description and for coated electrodes. The two spectra estimation segments 4 and 5 correspond to the spectral power graphs shown in FIGS. 13 and 14.

Figure 10:
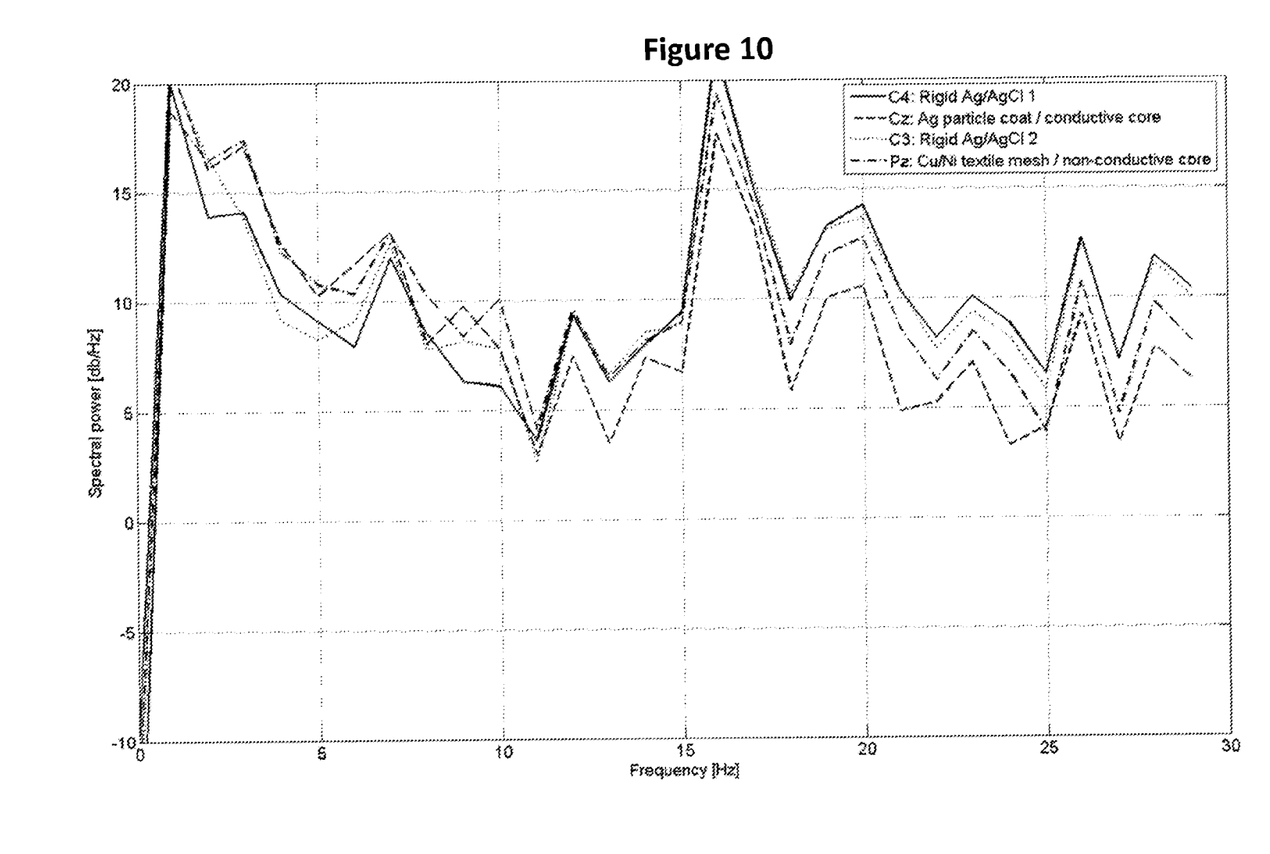
FIGS. 10, 11, 12, 13 and 14 show graphs of spectral power values from a plurality of electrodes for biopotential sensing in comparison to an exemplary electrode for biopotential sensing.

FIG. 10 shows a first graph of spectral power values from a plurality of electrodes for biopotential sensing in comparison to an exemplary electrode for biopotential sensing according to the present description, during the first spectra estimation segment of FIG. 8. The subject has the eyes open and the spectra shows a high noise level and no substantial difference between the plurality of electrodes for biopotential sensing used (rigid or flexible).

Figure 11:
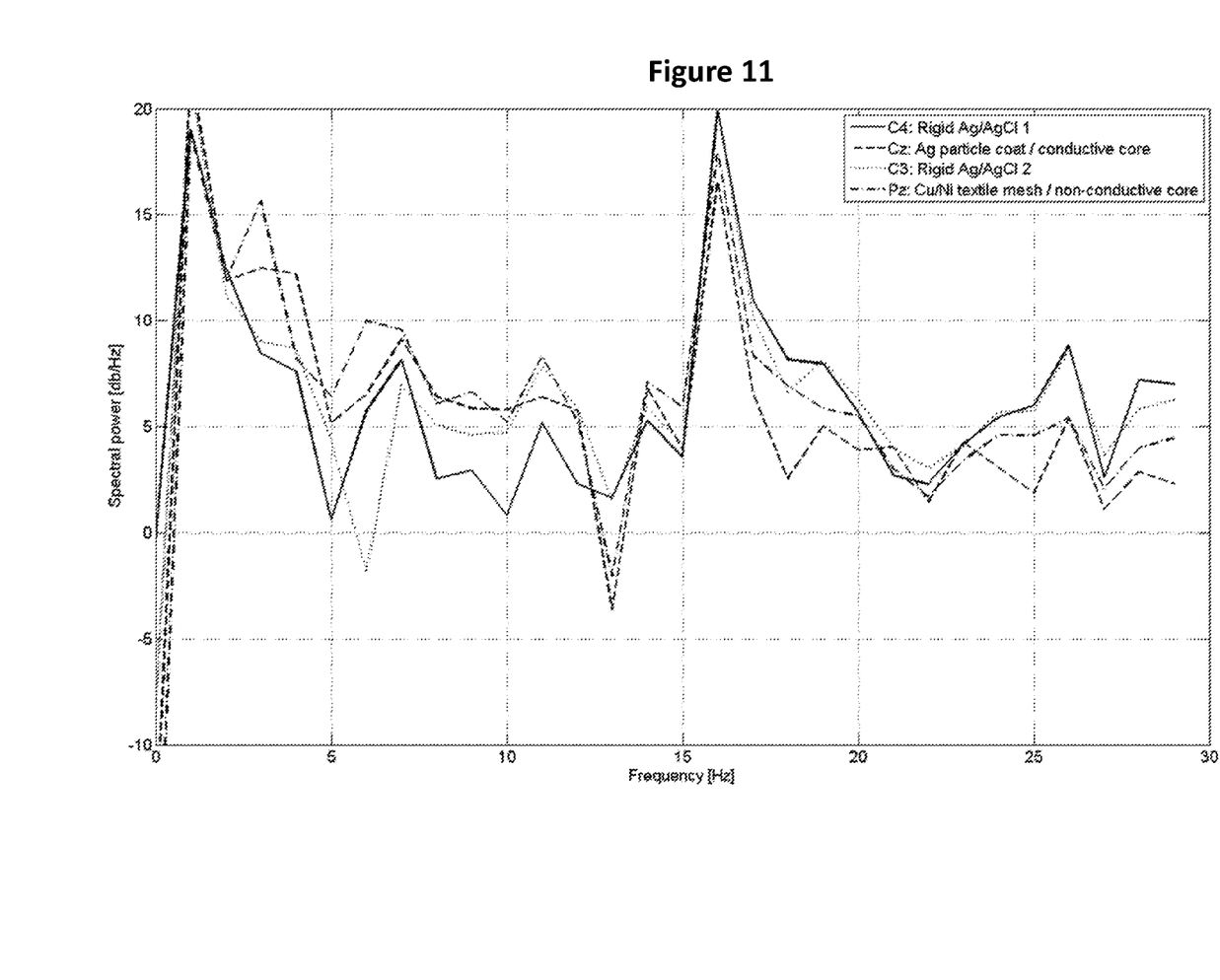

FIG. 11 shows a second graph of spectral power values from a plurality of electrodes for biopotential sensing in comparison to an exemplary electrode for biopotential sensing according to the present description, during the second spectra estimation segment of FIG. 8. The subject has the eyes open and the spectra shows decreased noise level and no substantial difference between the plurality of electrodes for biopotential sensing used (rigid or flexible).

Figure 12:
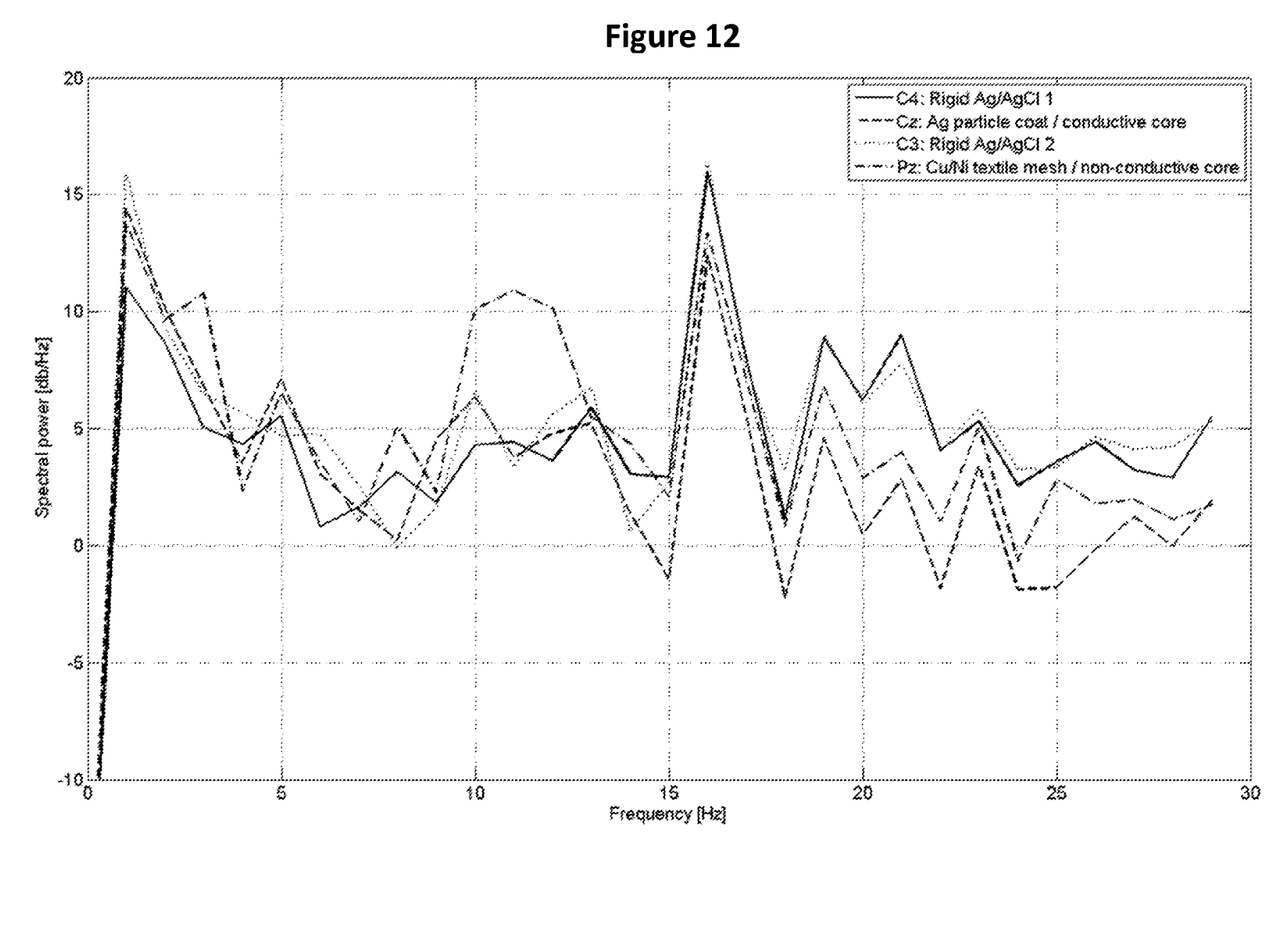

FIG. 12 shows a third graph of spectral power values from a plurality of electrodes for biopotential sensing in comparison to an exemplary electrode for biopotential sensing according to the present description, during the third spectra estimation segment of FIG. 8. The subject has the eyes closed, which increases the signal at 10-12 Hz. The spectra shows further decrease in noise level and no substantial difference between the plurality of electrodes for biopotential sensing used (rigid or flexible).

Figure 13:
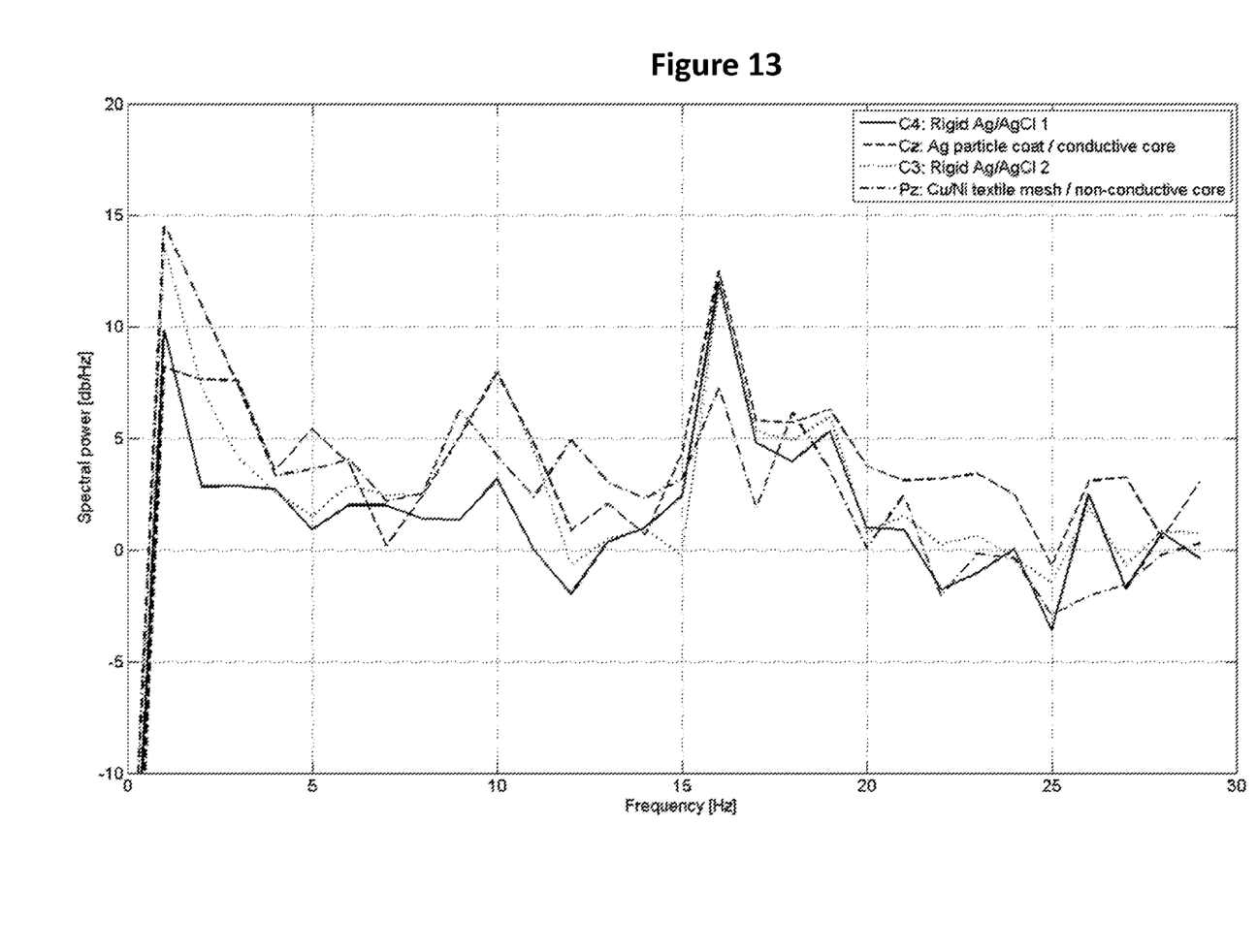

FIG. 13 shows a fourth graph of spectral power values from a plurality of electrodes for biopotential sensing in comparison to an exemplary electrode for biopotential sensing according to the present description, during the fourth spectra estimation segment of FIG. 9. The subject has the eyes closed and the spectra show a stable noise level and no substantial difference between the plurality of electrodes for biopotential sensing used (rigid or flexible).

Figure 14:
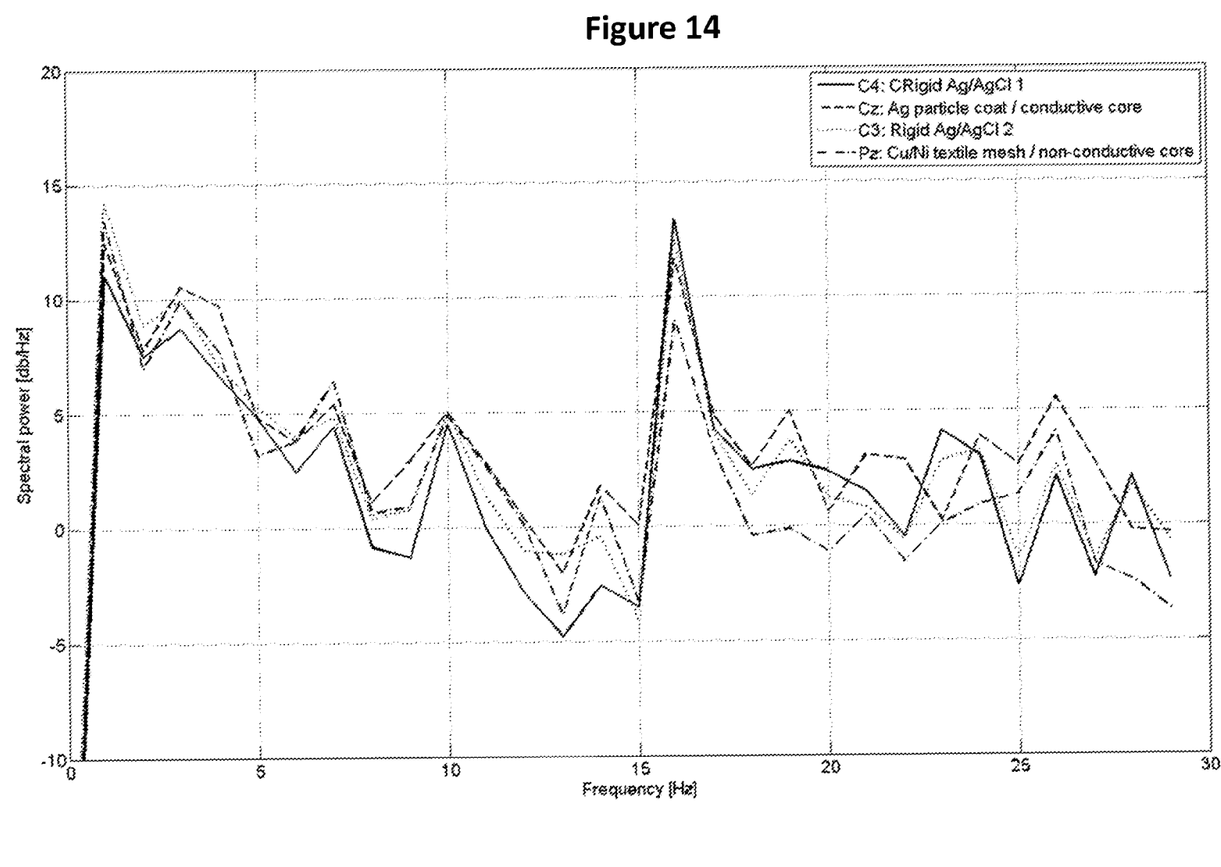

FIG. 14 shows a fifth graph of spectral power values from a plurality of electrodes for biopotential sensing in comparison to an exemplary electrode for biopotential sensing according to the present description, during the fifth spectra estimation segment of FIG. 9. The subject has the eyes open and the spectra show a stable noise level and no substantial difference between the plurality of electrodes for biopotential sensing used (rigid or flexible).

FIGS. 10 to 14 indicate environment noise around 16 Hz which may be present in all electrodes used. In summary, the quality of the EEG signal obtained using an exemplary electrode for biopotential sensing according to the present description comes close to current state of the art dry-contact rigid electrodes.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

What is claimed is:

1. An electrode for biopotential sensing comprising:
a main electrode base;
at least a plurality of contact pins protruding from the main electrode base and configured to make contact with a subject's skin, wherein each of the plurality of contact pins comprises a conductive mesh having an elongated pillar shape, wherein the conductive mesh comprises a woven fabric comprising a plurality of conductive wires or fibres designed for being flexible and ensuring conductivity of the pins; and
a tip configured to be in contact with the conductive mesh and the subject's skin, wherein the tip is covered with a non-polarizable electrode material.

2. The electrode for biopotential sensing according to claim 1 wherein the elongated pillar shape conductive mesh has a width between 1 mm and 2.5 mm and a length that is greater than the width.

3. The electrode for biopotential sensing according to claim 1 wherein the non-polarizable electrode material comprises at least one material containing ions that are also present in biological fluids.

4. The electrode for biopotential sensing according to claim 1 wherein the tip is substantially rigid, wherein the tip comprises a spherical, hemispherical, or conical shape.

5. The electrode for biopotential sensing according to claim 1 wherein the conductive mesh comprises a core, wherein at least one portion of the core conductive mesh is hollow.

6. The electrode for biopotential sensing according to claim 1 wherein each contact pin of the plurality of contact pins comprises two or more conductive meshes having an elongated pillar shape.

7. The electrode for biopotential sensing according to claim 1 wherein the conductive mesh comprises a core, wherein at least one portion of the core comprises a flexible core material.

8. The electrode for biopotential sensing according to claim 7 wherein the flexible core material comprises an elastic or compressible material.

9. The electrode for biopotential sensing according to claim 8, wherein the elastic or compressible material comprises at least one of: a foam or a polymer.

10. The electrode for biopotential sensing according to claim 7 wherein the flexible core material comprises additives so as to increase a conductivity of the material.

11. The electrode for biopotential sensing according to claim 1 wherein the main electrode base comprises a conductive material, or a non-conductive material comprising one or more conductors configured to make electrical contact with the conductive mesh.

12. The electrode for biopotential sensing according to claim 1 wherein the plurality of contact pins includes four or more pins.

13. A headset or biopotential monitoring system comprising an electrode for biopotential sensing according to claim 1.

14. An electrode for biopotential sensing comprising:
a main electrode base, wherein the electrode is configured for dry-contact biopotential sensing;
at least a plurality of contact pins protruding from the main electrode base and configured to make contact with a subject's skin, wherein each of the plurality of contact pins comprises a conductive mesh having an elongated pillar shape, wherein the conductive mesh comprises a woven fabric comprising a plurality of conductive wires or fibres designed for being flexible and ensuring conductivity of the pins; and
a tip configured to be in contact with the conductive mesh and the subject's skin, wherein the tip is covered with a non-polarizable electrode material.

15. The electrode for biopotential sensing according to claim 14 wherein the conductive mesh comprises a core, wherein at least one portion of the core is hollow.

16. The electrode for biopotential sensing according to claim 14 wherein the conductive mesh comprises a core, wherein at least one portion of the core comprises a flexible core material.

* * * * *